(12) United States Patent
Quick et al.

(10) Patent No.: US 9,259,237 B2
(45) Date of Patent: Feb. 16, 2016

(54) METHODS AND APPARATUS FOR TREATING PULMONARY EMBOLISM

(71) Applicant: Inceptus Medical, LLC, Aliso Viejo, CA (US)

(72) Inventors: Richard Quick, Mission Viejo, CA (US); Brian J. Cox, Laguna Niguel, CA (US); Paul Lubock, Monarch Beach, CA (US); Robert F. Rosenbluth, Laguna Niguel, CA (US)

(73) Assignee: INCEPTUS MEDICAL, LLC, Aliso Viejo, CA (US)

( * ) Notice: Subject to any disclaimer, the term of this patent is extended or adjusted under 35 U.S.C. 154(b) by 0 days.

(21) Appl. No.: 14/299,933

(22) Filed: Jun. 9, 2014

(65) Prior Publication Data

US 2015/0018859 A1    Jan. 15, 2015

Related U.S. Application Data

(60) Provisional application No. 61/949,953, filed on Mar. 7, 2014, provisional application No. 61/845,796, filed on Jul. 12, 2013.

(51) Int. Cl.
| | | |
|---|---|---|
| *A61B 17/14* | (2006.01) | |
| *A61B 17/3207* | (2006.01) | |
| *A61B 17/221* | (2006.01) | |
| *A61B 17/00* | (2006.01) | |
| *A61B 17/32* | (2006.01) | |
| *A61B 17/22* | (2006.01) | |

(52) U.S. Cl.
CPC ....... *A61B 17/320725* (2013.01); *A61B 17/221* (2013.01); *A61B 2017/00778* (2013.01); *A61B 2017/22034* (2013.01); *A61B 2017/320008* (2013.01)

(58) Field of Classification Search
USPC .......................................................... 606/128
See application file for complete search history.

(56) References Cited

U.S. PATENT DOCUMENTS

| | | |
|---|---|---|
| 3,435,826 A | 4/1969 | Fogarty |
| 3,923,065 A | 12/1975 | Nozick et al. |

(Continued)

FOREIGN PATENT DOCUMENTS

| | | |
|---|---|---|
| EP | 1849440 | 10/2007 |
| JP | 6190049 | 7/1994 |

(Continued)

OTHER PUBLICATIONS

Gibbs, et al., "Temporary Stent as a bail-out device during percutaneous transluminal coronay angioplasty: preliminary clinical experience," British Heart Journal, 1994, 71:372-377, Oct. 12, 1993 6 pgs.

(Continued)

*Primary Examiner* — Tuan V Nguyen
(74) *Attorney, Agent, or Firm* — Perkins Coie LLP

(57) ABSTRACT

A device and method for intravascular treatment of an embolism, and particularly a pulmonary embolism, is disclosed herein. One aspect of the present technology, for example, is directed toward a clot treatment device that includes a support member configured to extend through a delivery catheter and a plurality of clot engagement members positioned about the circumference of a distal portion of the support member. The individual clot engagement members can have a first portion and a second portion extending from the first portion, and the first portions can have a proximal region attached to the support member. In the deployed state, the individual second portions can extend from the distal region of one of the first portions and project radially outwardly relative to the support member in a curve that has a proximally extending section which defines a proximally facing concave portion.

13 Claims, 17 Drawing Sheets

(56) References Cited

U.S. PATENT DOCUMENTS

| | | | |
|---|---|---|---|
| 4,030,503 A | 6/1977 | Clark, III | |
| 4,650,466 A | 3/1987 | Luther | |
| 4,873,978 A | 10/1989 | Ginsburg | |
| 4,883,458 A | 11/1989 | Shiber | |
| 4,890,611 A | 1/1990 | Monfort et al. | |
| 5,011,488 A | 4/1991 | Ginsburg | |
| 5,059,178 A | 10/1991 | Ya | |
| 5,102,415 A | 4/1992 | Guenther et al. | |
| 5,129,910 A | 7/1992 | Phan et al. | |
| 5,192,286 A | 3/1993 | Phan et al. | |
| 5,192,290 A | 3/1993 | Hilal | |
| 5,370,653 A | 12/1994 | Cragg | |
| 5,476,450 A | 12/1995 | Ruggio | |
| 5,490,859 A | 2/1996 | Mische et al. | |
| 5,746,758 A | 5/1998 | Nordgren et al. | |
| 5,749,858 A | 5/1998 | Cramer | |
| 5,766,191 A | 6/1998 | Trerotola | |
| 5,800,525 A | 9/1998 | Bachinski et al. | |
| 5,827,304 A | 10/1998 | Hart | |
| 5,868,708 A | 2/1999 | Hart et al. | |
| 5,882,329 A | 3/1999 | Patterson et al. | |
| 5,972,019 A | 10/1999 | Engelson et al. | |
| 6,066,149 A | 5/2000 | Samson et al. | |
| 6,221,006 B1 | 4/2001 | Dubrul et al. | |
| 6,238,412 B1 | 5/2001 | Dubrul et al. | |
| 6,254,571 B1 | 7/2001 | Hart | |
| 6,306,163 B1 | 10/2001 | Fitz | |
| 6,383,205 B1 | 5/2002 | Samson et al. | |
| 6,454,741 B1 | 9/2002 | Muni et al. | |
| 6,454,775 B1 | 9/2002 | Demarais et al. | |
| 6,458,139 B1 | 10/2002 | Palmer et al. | |
| 6,511,492 B1 * | 1/2003 | Rosenbluth et al. | 606/159 |
| 6,514,273 B1 | 2/2003 | Voss et al. | |
| 6,544,279 B1 | 4/2003 | Hopkins et al. | |
| 6,605,102 B1 | 8/2003 | Mazzocchi et al. | |
| 6,635,070 B2 | 10/2003 | Leeflang et al. | |
| 6,645,222 B1 | 11/2003 | Parodi et al. | |
| 6,660,013 B2 | 12/2003 | Rabiner et al. | |
| 6,685,722 B1 | 2/2004 | Rosenbluth et al. | |
| 6,692,504 B2 | 2/2004 | Kurz et al. | |
| 6,699,260 B2 | 3/2004 | Dubrul et al. | |
| 6,767,353 B1 | 7/2004 | Shiber | |
| 6,994,092 B2 | 2/2006 | van der Burg et al. | |
| 7,004,954 B1 | 2/2006 | Voss et al. | |
| 7,052,500 B2 | 5/2006 | Bashiri et al. | |
| 7,128,073 B1 | 10/2006 | van der Burg et al. | |
| 7,179,273 B1 | 2/2007 | Palmer et al. | |
| 7,220,269 B1 | 5/2007 | Ansel et al. | |
| 7,244,243 B2 | 7/2007 | Lary | |
| 7,285,126 B2 | 10/2007 | Sepetka et al. | |
| 7,320,698 B2 | 1/2008 | Eskuri | |
| 7,578,830 B2 | 8/2009 | Kusleika et al. | |
| 7,727,189 B2 | 6/2010 | VanTassel et al. | |
| 7,938,820 B2 | 5/2011 | Webster et al. | |
| 7,993,302 B2 | 8/2011 | Hebert et al. | |
| 7,993,363 B2 | 8/2011 | Demond et al. | |
| 8,043,313 B2 | 10/2011 | Krolik et al. | |
| 8,052,640 B2 | 11/2011 | Fiorella et al. | |
| 8,066,757 B2 | 11/2011 | Ferrera et al. | |
| 8,070,791 B2 | 12/2011 | Ferrera et al. | |
| 8,075,510 B2 | 12/2011 | Aklog et al. | |
| 8,100,935 B2 | 1/2012 | Rosenbluth et al. | |
| 8,118,829 B2 | 2/2012 | Carrison et al. | |
| 8,246,641 B2 | 8/2012 | Osborne et al. | |
| 8,784,434 B2 | 7/2014 | Rosenbluth et al. | |
| 8,852,205 B2 * | 10/2014 | Brady et al. | 606/114 |
| 8,968,330 B2 | 3/2015 | Rosenbluth et al. | |
| 2002/0072765 A1 | 6/2002 | Mazzocchi et al. | |
| 2002/0123802 A1 | 9/2002 | Snyders | |
| 2002/0147458 A1 | 10/2002 | Hiblar et al. | |
| 2004/0073243 A1 * | 4/2004 | Sepetka et al. | 606/159 |
| 2004/0215167 A1 | 10/2004 | Belson | |
| 2005/0119668 A1 * | 6/2005 | Teague et al. | 606/127 |
| 2005/0137692 A1 | 6/2005 | Haug et al. | |
| 2005/0283224 A1 | 12/2005 | King | |
| 2006/0247680 A1 | 11/2006 | Amplatz et al. | |
| 2006/0253145 A1 | 11/2006 | Lucas | |
| 2006/0282111 A1 | 12/2006 | Morsi | |
| 2007/0106311 A1 | 5/2007 | Wallace et al. | |
| 2007/0118165 A1 * | 5/2007 | DeMello et al. | 606/159 |
| 2007/0161963 A1 | 7/2007 | Smalling | |
| 2007/0179513 A1 | 8/2007 | Deutsch | |
| 2007/0191866 A1 | 8/2007 | Palmer et al. | |
| 2007/0198028 A1 | 8/2007 | Miloslavski et al. | |
| 2007/0208361 A1 | 9/2007 | Okushi et al. | |
| 2007/0208367 A1 | 9/2007 | Fiorella et al. | |
| 2007/0208412 A1 | 9/2007 | Elmaleh | |
| 2007/0213753 A1 | 9/2007 | Waller | |
| 2007/0255252 A1 | 11/2007 | Mehta | |
| 2008/0015541 A1 | 1/2008 | Rosenbluth et al. | |
| 2008/0167678 A1 | 7/2008 | Morsi | |
| 2008/0228209 A1 | 9/2008 | DeMello et al. | |
| 2008/0269798 A1 | 10/2008 | Ramzipoor et al. | |
| 2008/0275540 A1 | 11/2008 | Wen | |
| 2009/0054918 A1 | 2/2009 | Henson | |
| 2009/0062841 A1 | 3/2009 | Amplatz et al. | |
| 2009/0099647 A1 | 4/2009 | Glimsdale et al. | |
| 2009/0112309 A1 | 4/2009 | Jaramillo et al. | |
| 2009/0163846 A1 | 6/2009 | Aklog et al. | |
| 2009/0182362 A1 | 7/2009 | Thompson et al. | |
| 2009/0222076 A1 | 9/2009 | Figulla et al. | |
| 2009/0275974 A1 | 11/2009 | Marchand et al. | |
| 2009/0292307 A1 | 11/2009 | Razack | |
| 2010/0030244 A1 | 2/2010 | Woolfson et al. | |
| 2010/0036474 A1 | 2/2010 | Bergheim | |
| 2010/0114113 A1 | 5/2010 | Dubrul et al. | |
| 2010/0114152 A1 | 5/2010 | Shukla | |
| 2010/0249815 A1 | 9/2010 | Jantzen et al. | |
| 2010/0256723 A1 | 10/2010 | Murray | |
| 2010/0318178 A1 | 12/2010 | Rapaport et al. | |
| 2011/0060212 A1 | 3/2011 | Slee et al. | |
| 2011/0146361 A1 | 6/2011 | Davidson et al. | |
| 2011/0152993 A1 | 6/2011 | Marchand et al. | |
| 2011/0190806 A1 | 8/2011 | Wittens | |
| 2011/0208234 A1 | 8/2011 | Mazzocchi et al. | |
| 2011/0213290 A1 | 9/2011 | Chin et al. | |
| 2011/0213403 A1 | 9/2011 | Aboytes | |
| 2011/0224707 A1 | 9/2011 | Miloslavski et al. | |
| 2011/0251629 A1 | 10/2011 | Galdonik et al. | |
| 2012/0089216 A1 | 4/2012 | Rapaport et al. | |
| 2012/0101510 A1 | 4/2012 | Lenker et al. | |
| 2012/0143239 A1 | 6/2012 | Aklog et al. | |
| 2012/0165919 A1 | 6/2012 | Cox et al. | |
| 2012/0179181 A1 | 7/2012 | Straub et al. | |
| 2012/0232655 A1 | 9/2012 | Lorrison et al. | |
| 2012/0271231 A1 | 10/2012 | Agrawal | |
| 2012/0330347 A1 | 12/2012 | Becking et al. | |
| 2014/0005713 A1 | 1/2014 | Bowman | |
| 2015/0005811 A1 | 1/2015 | Lubock et al. | |

FOREIGN PATENT DOCUMENTS

| | | |
|---|---|---|
| JP | 2004097807 | 4/2004 |
| JP | 2005230132 | 9/2005 |
| JP | 2005323702 | 11/2005 |
| JP | 2006094876 | 4/2006 |
| WO | WO-9717889 | 5/1997 |
| WO | WO-0043062 | 7/2000 |
| WO | WO-2005046736 | 5/2005 |
| WO | WO-2006074032 | 7/2006 |
| WO | WO-2006110186 | 10/2006 |
| WO | WO-2006128193 | 11/2006 |
| WO | WO-2007092820 | 8/2007 |
| WO | WO-2008066881 | 6/2008 |
| WO | WO-2008150346 | 12/2008 |
| WO | WO-2009155571 | 12/2009 |
| WO | WO-2010006061 | 1/2010 |
| WO | WO-2010010545 | 1/2010 |
| WO | WO-2010023671 | 3/2010 |
| WO | WO-2010049121 | 5/2010 |
| WO | WO-2010102307 | 9/2010 |
| WO | WO-2011027002 | 3/2011 |
| WO | WO-2011054531 | 5/2011 |
| WO | WO-2011057002 | 5/2011 |

(56) References Cited

FOREIGN PATENT DOCUMENTS

| WO | WO-2011057087 | 5/2011 |
|---|---|---|
| WO | WO-2012009675 | 1/2012 |
| WO | WO-2012/065748 | 5/2012 |
| WO | WO-2013028579 | 2/2013 |
| WO | WO-2013104721 | 7/2013 |
| WO | WO-2014047650 | 3/2014 |
| WO | WO-2014081892 | 5/2014 |
| WO | WO-2015006782 | 1/2015 |
| WO | WO-2015061365 | 4/2015 |

OTHER PUBLICATIONS

Goldhaber, S., "Advanced treatment strategies for acute pulmonary embolism, including thrombolysis and embolectomy", Journal of Thrombosis and Haemostasis, 2009: 7 (Suppl. 1): 322-327.
Goldhaber, S. et al. "Percutaneous Mechanical Thrombectomy for Acute Pulmonary Embolism—A Double-Edged Sword", American College of CHEST Physicians, Aug. 2007: 132:2, 363-372.
Gupta, S. et al., "Acute Pulmonary Embolism Advances in Treatment", JAPI, Association of Physicians India, Mar. 2008, vol. 56, 185-191.
International Search Report for International App. No. PCT/US13/61470, mailed Jan. 17, 2014, 2 pages.
International Search Report for International App. No. PCT/US13/71101, mailed Mar. 31, 2014, 4 pages.
Konstantinides, S. et al., "Pulmonary embolism hotline 2012—Recent and expected trials", Thrombosis and Haemostasis, Jan. 9, 2013:33; 43-50, Center for Thrombosis and Haemostasis, Johannes Gutenberg University Medical Center, Mainz, Germany.
Konstantinides, S. et al., "Pulmonary embolism: risk assessment and management", European Society of Cardiology; European Heart Journal, Sep. 7, 2012:33, 3014-3022.
Kucher, N. et al., "Percutaneous Catheter Thrombectomy Device for Acute Pulmonary Embolism: in Vitro and In Vivo Testing", Circulation, Sep. 2005:112:e28-e32.
Kucher, N., "Catheter Interventions in Massive Pulmonary Embolism", CardiologyRounds, Mar. 2006 vol. 10, Issue 3, 6 pages.
Kucher, N. et al., "Management of Massive Pulmonary Embolism", Radiology, Sep. 2005:236:3 852-858.
Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.
Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254, Northbrook, IL, USA.
Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.
Lee, L. et al, "Massive pulmonary embolism: review of management strategies with a focus on catheter- based techniques", Expert Rev. Cardiovasc. Ther. 8(6), 863-873 (2010).
Liu, S. et al, "Massive Pulmonary Embolism: Treatment with the Rotarex Thrombectomy System", Cardiovascular Interventional Radiology; 2011: 34:106-113.
Muller-Hulsbeck, S. et al. "Mechanical Thrombectomy of Major and Massive Pulmonary Embolism with Use of the Amplatz Thrombectomy Device", Investigative Radiology Jun. 2001:36:6:317-322.
Non-Final Office Action for U.S. Appl. No. 13/843,742, Mailed Sep. 13, 2013, 16 pages.
Notice of Allowance for U.S. Appl. No. 13/843,742, mailed Mar. 12, 2014, 13 pages.
Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs).
Schmitz-Rode, T. et al., "Massive Pulmonary Embolism: Percutaneous Emergency Treatment by Pictail Rotation Catheter", JACC Journal of the American College of Cardiology, Aug. 2000:36:2:375-380, Elsevier Science, Inc., New York NY, USA.
Tapson, V., "Acute Pulmonary Embolism", The New England Journal of Medicine, Mar. 6, 2008:358:2037-52.
Truong et al., "Mechanical Thrombectomy of Iliocaval Thrombosis Using a Protective Ex andable Sheath," Cardiovasc Intervent Radiol 27-254-258, 2004, 5 pgs.
Turk et al., "ADAPT FAST study: a direct aspiration first pass technique for acute stroke thrombectomy." J Neurolntervent Surg, vol. 6, 2014, 6 pages.
Uflacker, R., "Interventional Therapy for Pulmonary Embolism", Journal of Vascular and Interventional Radiology Feb. 2001: 12:147-164.
Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.
International Search Report and Written Opinion for International App. No. PCT/US2014/046567, mailed Nov. 3, 2014, 13 pages.
European Search Report and Written Opinion for European App. No. 12801855, completed Dec. 17, 2014, 7 pages.
International Search Report and Written Opinion for Application PCT/US12/43885. Date of Mailing Dec. 26, 2012 pp. 14.
International Search Report and Written Opinion for Application PCT/US12/51502. Date of Mailing Oct. 25, 2012 pp. 11.
International Search Report and Written Opinion for Application PCT/US12/67479. Date of Mailing Feb. 25, 2013 pp. 12.
International Search Report and Written Opinion for Application PCT/US13/20381. Date of Mailing Apr. 8, 2013 pp. 13.
International Search Report and Written Opinion for Application PCT/US13/37484. Date of Mailing Sep. 12, 2013 pp. 12.
International Search Report and Written Opinion for International Application No. PCT/US2014/029210, mailed Aug. 12, 2014, 15 pages.
Schmitz-Rode et al., "Temporary Pulmonary Stent Placement as Emergency Treatment of Pulmonary Embolism," Journal of the American College of Cardiology, vol. 48, No. 4, 2006, 5 pgs.
Final Office Action for U.S. Appl. No. 14/299,997, mailed Dec. 24, 2014, 11 pages.
Non Final Office Action for U.S. Appl. No. 14/299,997, mailed Sep. 3, 2014, 9pages.
Notice of Allowance for U.S. Appl. No. 14/288,778, mailed Dec. 23, 2014, 12 pages.
International Search Report and Written Opinion for International App. No. PCT/US2014/061645, mailed Jan. 23, 2015, 15 pages.
Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.
Spiotta, A et al., "Evolution of thrombectomy approaches and devices for acute stroke: a technical review." J Neurolntervent Surg 2015, 7, pp. 7 pages.
Svilaas, T. et al., "Thrombus Aspiration During Primary Percutaneous Coronary Intervention." The New England Journal of Medicine, 2008, vol. 358, No. 6, 11 pages.
The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: 9 pages.
International Search Report and Written Opinion for International Application No. PCT/US2015/034987, mailed Sep. 17, 2015, 12 pages.
European Search Report and Written Opinion for European App. No. 12825306.9, mailed May 28, 2015, 6 pages.

* cited by examiner

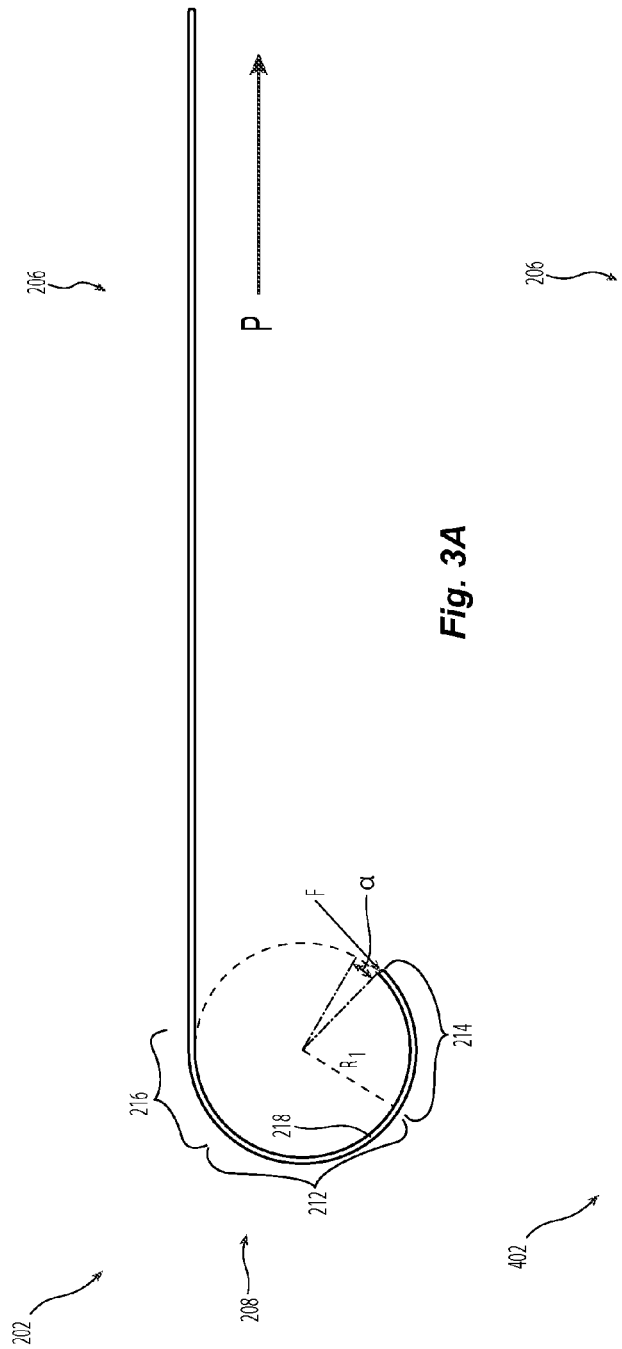
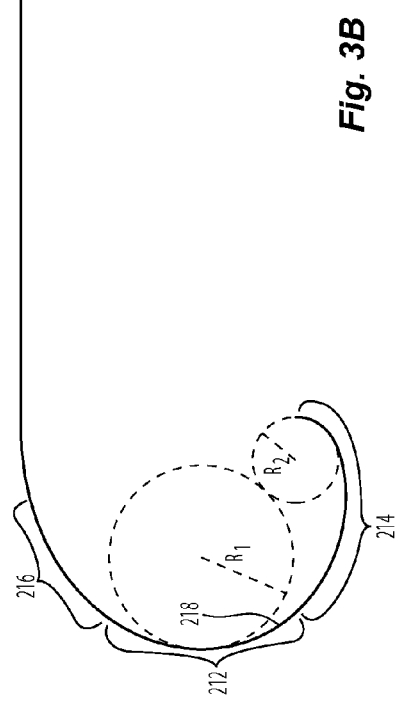
Fig. 3A
Fig. 3B

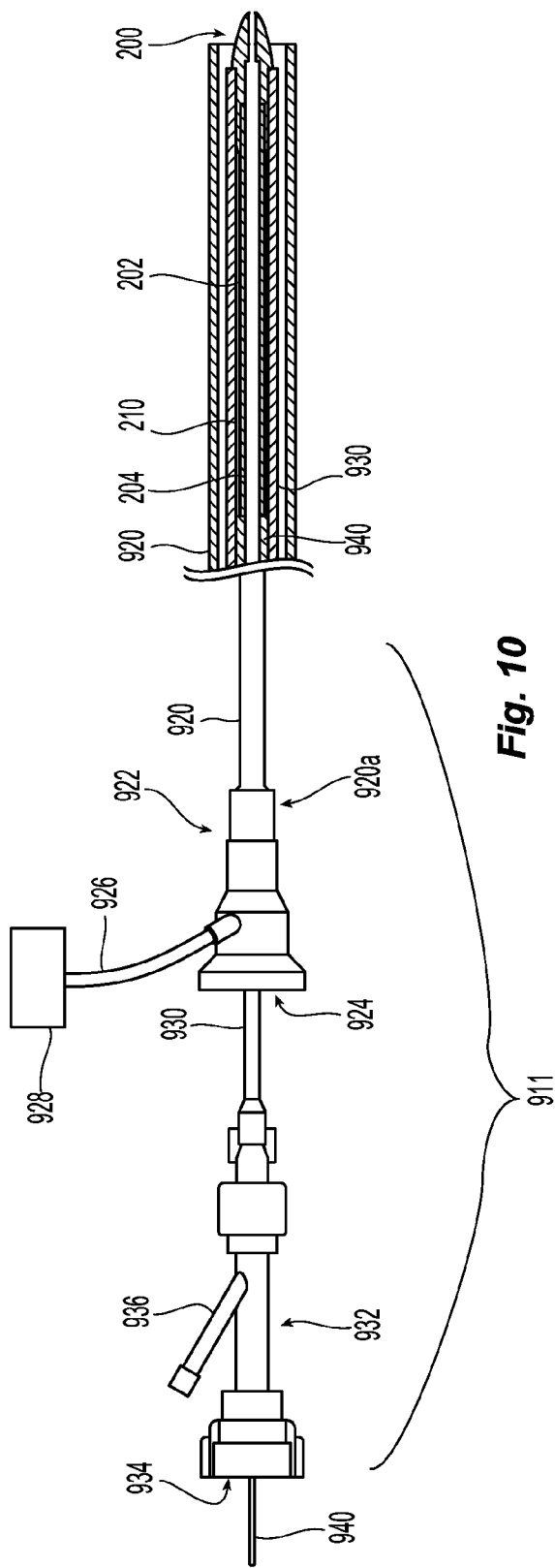

ered used in combination with one another. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

METHODS AND APPARATUS FOR TREATING PULMONARY EMBOLISM

CROSS-REFERENCE TO RELATED APPLICATIONS

The present application claims the benefit of U.S. Provisional Patent Application No. 61/949,953 filed Mar. 7, 2014, entitled "METHODS AND APPARATUS FOR TREATING EMBOLISM," and U.S. Provisional Patent Application No. 61/845,796 filed Jul. 12, 2013, entitled "DEVICES AND METHODS FOR TREATMENT OF VASCULAR OCCLUSIONS (V.3)", both of which are incorporated herein by reference in their entireties.

TECHNICAL FIELD

The present technology relates generally to devices and methods for intravascular treatment of emboli within a blood vessel of a human patient. Many embodiments of the technology relate to the intravascular treatment of a pulmonary embolism.

BACKGROUND

Thromboembolism occurs when a thrombus or blood clot trapped within a blood vessel breaks loose and travels through the blood stream to another location in the circulatory system, resulting in a clot or obstruction at the new location. As shown schematically in FIG. 1, when a clot C forms in the venous circulation V, it often travels to the lungs L via the heart H and lodges within a pulmonary blood vessel PV causing a pulmonary embolism PE. A pulmonary embolism PE can decrease blood flow through the lungs L, which in turn causes decreased oxygenation of the lungs L, heart H and rest of the body. Moreover, pulmonary embolisms can cause the right ventricle RV of the heart H to pump harder to provide sufficient blood to the pulmonary blood vessels PV, which can cause right ventricle RV dysfunction (dilation), and heart failure in more extreme cases.

Conventional approaches to treating thromboembolism and/or pulmonary embolism include clot reduction and/or removal. For example, anticoagulants can be introduced to the affected vessel to prevent additional clots from forming, and thrombolytics can be introduced to the vessel to at least partially disintegrate the clot. However, such agents typically take a prolonged period of time (e.g., hours, days, etc.) before the treatment is effective and in some instances can cause hemorrhaging. Transcatheter clot removal devices also exist, however, such devices are typically highly complex, prone to cause trauma to the vessel, hard to navigate to the pulmonary embolism site, and/or expensive to manufacture. Conventional approaches also include surgical techniques that involve opening the chest cavity and dissecting the pulmonary vessel. Such surgical procedures, however, come with increased cost, procedure time, risk of infection, higher morbidity, higher mortality, and recovery time. Accordingly, there is a need for devices and methods that address one or more of these deficiencies.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIGS. 3A-3C are isolated, enlarged side views of clot engagement members in a deployed state configured in accordance with embodiments of the present technology.

FIG. 10 is a side partial cross-sectional view of a delivery system configured in accordance an embodiment of the present technology.

DETAILED DESCRIPTION

Specific details of several embodiments of clot treatment devices, systems and associated methods in accordance with the present technology are described below with reference to FIGS. 2A-11K. Although many of the embodiments are described below with respect to devices, systems, and methods for treating a pulmonary embolism, other applications and other embodiments in addition to those described herein are within the scope of the technology. Additionally, several other embodiments of the technology can have different states, components, or procedures than those described herein. Moreover, it will be appreciated that specific elements, substructures, advantages, uses, and/or other features of the embodiments described with reference to FIGS. 2A-11K can be suitably interchanged, substituted or otherwise configured with one another in accordance with additional embodiments of the present technology. Furthermore, suitable elements of the embodiments described with reference to FIGS. 2A-11K can be used as standalone and/or self-contained devices. A person of ordinary skill in the art, therefore, will accordingly understand that the technology can have other embodiments with additional elements, or the technology can have other embodiments without several of the features shown and described below with reference to FIGS. 2A-11K.

With regard to the terms "distal" and "proximal" within this description, unless otherwise specified, the terms can reference a relative position of the portions of a clot treatment device and/or an associated delivery device with reference to an operator and/or a location in the vasculature.

I. Selected Embodiments of Clot Treatment Devices

Figure 1:
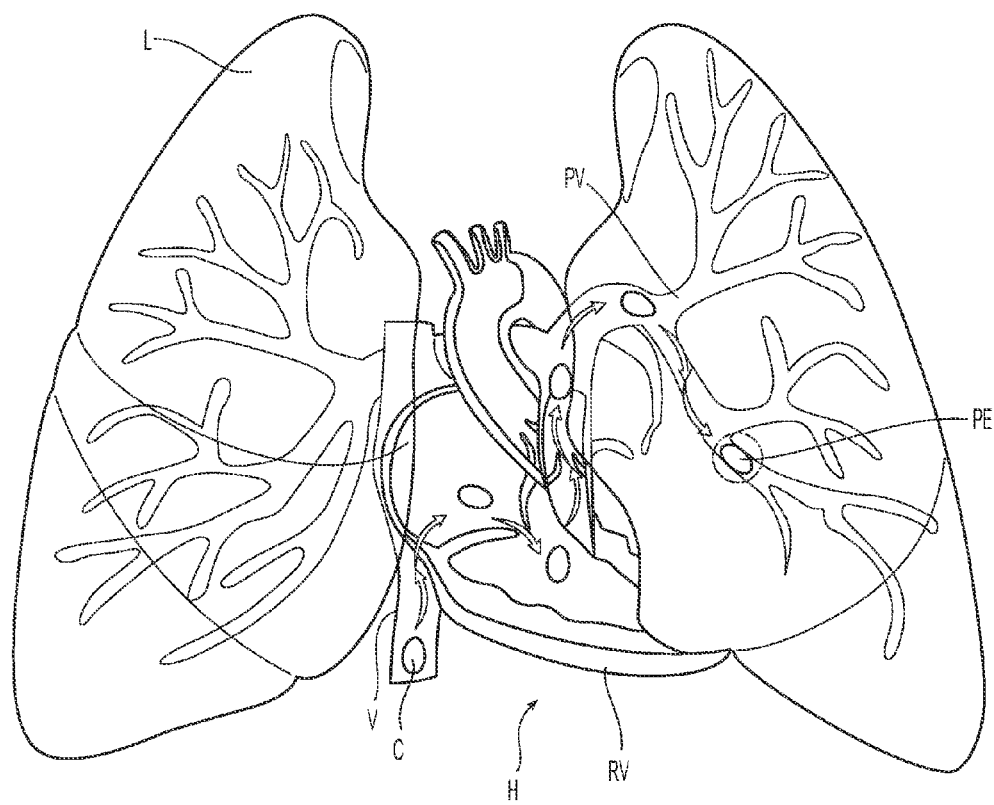
FIG. 1 is a schematic illustration of an embolism traveling through the heart and forming an embolism in a pulmonary vessel.
Figure 2A:
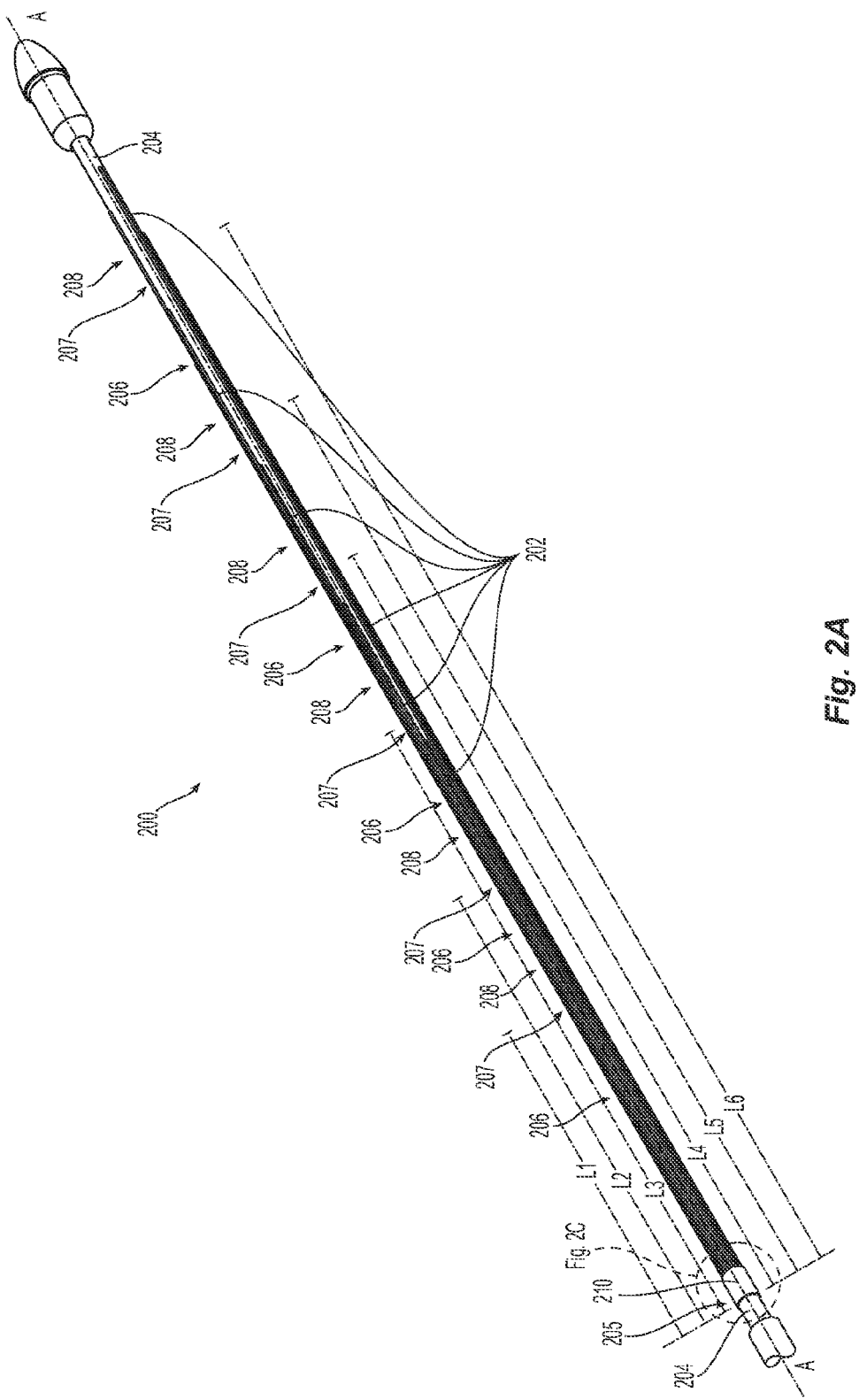
FIG. 2A is a perspective view of one embodiment of a clot treatment device in a collapsed or delivery state configured in accordance with an embodiment of the present technology.
Figure 2B:
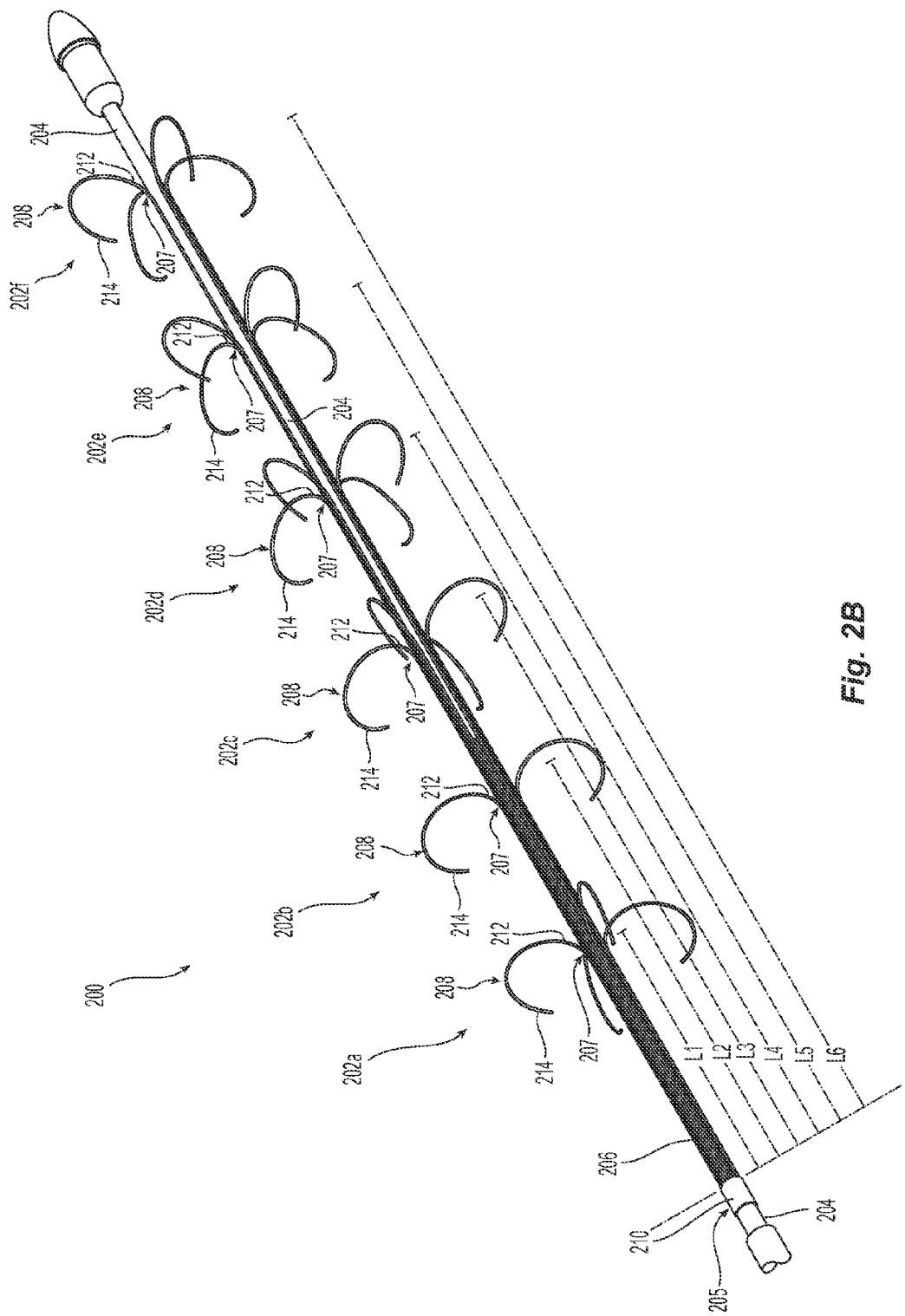
FIG. 2B is a perspective view of the clot treatment device of FIG. 2A in a deployed state configured in accordance with an embodiment of the present technology.

FIG. 2A is a perspective view of one embodiment of a clot treatment device 200 ("the device 200") in a low-profile or delivery state, and FIG. 2B is a perspective view of the device 200 in an unrestricted expanded or deployed state that is well suited for removing clot material from a blood vessel (e.g., a pulmonary blood vessel). Referring to FIGS. 2A and 2B together, the device 200 can include a support member 204 and a plurality of clot engagement members 202 positioned about the circumference of the support member 204. As best shown in FIG. 2B, the individual clot engagement members 202 can include a first portion 206 having a proximal region 205 and a distal region 207, and a second portion 208 extending from the distal region 207 of the first portion 206. In the delivery state, as shown in FIG. 2A, the clot engagement members 202 can be generally linear and extend generally parallel to the support member 204. In the expanded state, as shown in FIG. 2B, the second portions 208 can project radially outwardly relative to the support member 204 in a curved shape. The second portions 208 can have a proximally facing section 212 which defines a proximally facing concave portion, and, in some embodiments, the second portions 208 can further include an end section 214 that curves radially inwardly from the proximally facing section 212. When deployed within a blood vessel adjacent to clot material, the clot engagement members 202 are configured to penetrate the clot material along an arcuate path and hold clot material to the device 200, as discussed in greater detail below with reference to FIGS. 10-11K.

Figure 2C:
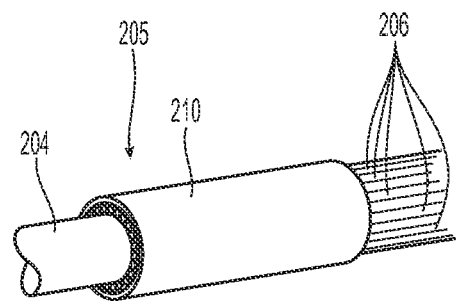
FIG. 2C is an enlarged view of a portion the clot treatment device shown in FIG. 2A.

FIG. 2C is an enlarged view of a portion of the device 200 of FIG. 2A showing that the device 200 can include a hub 210 that couples the proximal regions 205 of the first portions 206 to the support member 204. The first portions 206 can extend distally from their proximal regions 205 in a longitudinal direction along the length of the support member 204 to their distal regions 207, and the distal regions 207 can be free to move relative to the support member 204. As such, the first portions 206 can be cantilevered portions of the clot engagement members 202 that enable the clot engagement members 202 to flex and move independently of the support member 204 in response to forces present within the blood vessel, such as blood flow, gravity, and/or the local anatomy. The first portions 206 can be sufficiently rigid to maintain a generally linear shape along their respective lengths, yet flexible enough to bend and/or flex about the hub 210. For example, in some instances, in response to local forces, one or more of the distal regions 207 of the first portions 206 can be spaced radially apart from the support member 204 such that one or more first portions 206 forms an angle with the support member 204.

Referring back to FIGS. 2A and 2B, the first portions 206 of different clot engagement members 202 can have different lengths such that the second portions 208 of at least two clot engagement members extend radially outwardly at different locations along the length of the support member 204. For example, as best shown in FIG. 2B, the clot treatment device 200 can include a first group 202a of clot engagement members 202 having first portions 206 with a first length L1, a second group 202b of clot engagement members 202 having first portions 206 with a second length L2 greater than the first length L1, a third group of clot engagement members 202c having first portions 206 with a third length L3 greater than the second length L2, a fourth group of clot engagement members 202d having first portions 206 with a fourth length L4 greater than the third length L3, a fifth group of clot engagement members 202e having first portions 206 with a fifth length L5 greater than the fourth length L4, and a sixth group of clot engagement members 202f having first portions 206 with a sixth length L6 greater than the fifth length L5. It will be appreciated that although six groups of clot engagement members are shown in FIGS. 2A and 2B, in other embodiments the clot treatment device can have more or fewer than six groups (e.g., one group, two groups, three groups, seven groups, ten groups, etc.) and/or the lengths of all or some of the first portions 206 can be the same or different.

Moreover, the second portions 208 of the first group 202a of clot engagement members 202 extend radially outward at a first area of the support member 204, the second portions 208 of the second group 202b of the clot engagement members 202 extend radially outward from a second area of the support member 204, the second portions 208 of the third group 202c of clot engagement members 202 extend radially outward from a third area of the support member 204, the second portions 208 of the fourth group 202d of clot engagement members 202 extend radially outward from a fourth area of the support member 204, the second portions 208 of the fifth group 202e of clot engagement members 202 extend radially outward from a fifth area of the support member 204, and the second portions 208 of the sixth group 202f of clot engagement members 202 extend radially outward from a sixth area of the support member 204. It will be appreciated that although six areas of clot engagement members are shown in FIGS. 2A and 2B, in other embodiments the clot treatment device can have more or fewer than six areas (e.g., one area, two areas, three areas, five areas, nine areas, etc.).

Figure 2D:
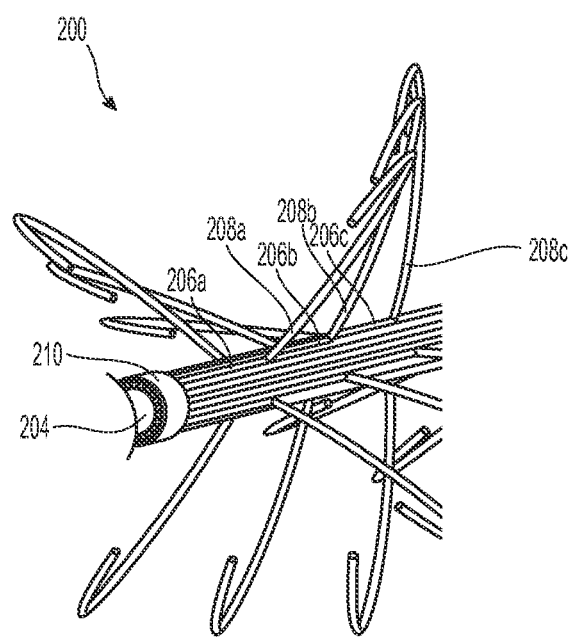
FIG. 2D is an axial-perspective view of a portion of the clot treatment device shown in FIG. 2A.

FIG. 2D is an enlarged, axial-perspective view of a portion of the device 200 in which the groups of clot engagement members 202a-f (only the first, second and third groups 202a-c shown) are arranged about the circumference of the support member 204 such that the second portions (labeled 208a-c) of adjacent groups 202a-c are circumferentially offset from one another. As such, in the embodiment shown in FIG. 2D, the second portions 208 of adjacent groups of clot engagement members 202a-f are not circumferentially aligned, and thus can engage the clot material at different circumferential positions along the length of the clot material.

FIG. 3A is a side view of a clot engagement member 202 in the expanded state. Individual clot engagement members can be made from a shape memory material such that, when unconstrained, assume a preformed curved shape. As shown in FIG. 3A, the second portion 208 can have an arcuate shape that includes an outwardly extending section 216, the proximally facing section 212 extending from the outwardly extending section 216, and the end section 214 extending from the proximally facing section 212. In one embodiment, the demarcation between the proximally facing section 212 and the end section 214 occurs at an apex 218 of the second portion 208. The proximally facing section 212 is configured to retain clot material with the clot engagement member 202 as the device 200 is pulled proximally through the vessel (arrow P), and the apex 218 provides a smooth curve that can atraumatically slide along the vessel wall as the device 200 is pulled proximally through the vessel. In the embodiment shown in FIG. 3A, the second portion 208 of the clot treatment device 200 can have a single or constant radius of curvature $R_1$. In other embodiments, such as the clot engagement member 402 shown in FIG. 3B, the second portions 208 can have a plurality of radii of curvature, such as a first region with a first radius of curvature $R_1$ and a second region with a second radius of curvature $R_2$. In the embodiment shown in FIGS. 2A-2D, the second portions 208 of the clot engagement members 202 have a single radius of curvature that is the same for all of the clot engagement members 202. In other embodiments, the device 200 can have a first group of second portions with a constant radius of curvature and a second group of second portions with a plurality of radii of curvature. Moreover, in additional embodiments the device 200 can include a first group of second portions having a first radius of curvature and a second group of second portions having a second radius of curvature different than the first radius of curvature. In some embodiments, the radius $R_1$ of the clot engagement members 202 can be between about 1.5 mm and about 12 mm, and in some embodiments, between about 2 mm and about 12 mm.

Figure 3C:
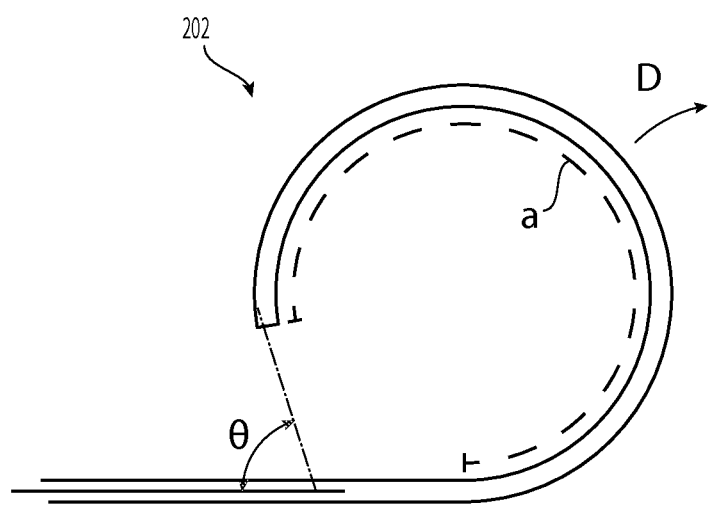

As shown in FIG. 3C, the arc length a of the clot engagement members 202 may be substantially greater than 180 degrees to provide several benefits in performance of clot engagement and retrieval. In particular, a greater arc length a can provide improved clot engagement during retraction when resistance due to clot friction and interference with the vessel wall deflects the clot engagement member 202 distally (arrow D). A greater arc length a may provide more deflection and/or unravelling or straightening of the arcuate shape without loss of engagement with the clot. In some embodiments, the arc length a of the clot engagement members 202 can be greater than about 200 degrees. In some embodiments the arc length a of the clot engagement members 202 may be between about 200 degrees and 340 degrees and between about 240 degrees and 300 degrees in other embodiments. It can be advantageous to keep the arc length a under about 360 degrees so as to avoid overlap of the clot engagement member 202. Greater arc length a can allow for the use of smaller clot engagement member filaments or wires that may be particularly beneficial for minimization of the collapsed profile of the device. Greater arc length a can also allow for a larger total number of clot engagement members 202 that also enhance the ability of the device to remove embolic material from a vessel. Moreover, in some embodiments, the distal end of the clot engagement members 202 may define an angle with respect to the axis of the support member and/or the straight portion of the engagement members (as shown in FIG. 3C). This angle may be between about 30 degrees and about 90 degrees, and in some embodiments between about 40 degrees and about 80 degrees.

The clot engagement members 202 can be made from a variety of materials. In a particular embodiment, the clot engagement members 202 comprise a material with sufficient elasticity to allow for repeated collapse into an appropriately sized catheter and full deployment in a blood vessel. Such suitable metals can include nickel-titanium alloys (e.g., Nitinol), platinum, cobalt-chrome alloys, Elgiloy, stainless steel, tungsten, titanium and/or others. Polymers and metal/polymer composites can also be utilized in the construction of the clot engagement members. Polymer materials can include Dacron, polyester, polyethylene, polypropylene, nylon, Teflon, PTFE, ePTFE, TFE, PET, TPE, PLA silicone, polyurethane, polyethylene, ABS, polycarbonate, styrene, polyimide, PEBAX, Hytrel, polyvinyl chloride, HDPE, LDPE, PEEK, rubber, latex and the like. In some embodiments, the clot engagement members 202 may comprise an environmentally responsive material, also known as a smart material. Smart materials are designed materials that have one or more properties that can be significantly changed in a controlled fashion by external stimuli, such as stress, temperature, moisture, pH, electric or magnetic fields.

In some embodiments, portions of the exterior surfaces of the support member 204 and/or clot engagement members 202 may be textured, or the exterior surfaces can include microfeatures configured to facilitate engagement or adhesion of thrombus material (e.g., ridges, bumps, protrusions, grooves, cut-outs, recesses, serrations, etc.). In some embodiments, the clot engagement members 202 may be coated with one or more materials to promote platelet activation or adhesion of thrombus material. Adhesion of thrombi to clot engagement members 202 may facilitate capture and/or removal.

In some embodiments, the clot treatment device 200 can include between about 8 and about 80 clot engagement members 202, and in some embodiments, between about 12 and about 60 clot engagement members 202. In a particular embodiment, the clot treatment device 200 can include between about 16 and about 40 clot engagement members 202. The clot engagement members 202 can individually have one consistent diameter or have a variety of diameters (among the members 202) along their lengths. In addition, an individual clot engagement member 202 may have a tapered or varying diameter along its length to provide desired mechanical characteristics. The average diameter of the clot engagement members 202 can be between about 0.1 mm to about 0.2 mm in some embodiments and in a particular embodiment, between about 0.12 mm and 0.16 mm.

In any of the embodiments described herein, the clot engagement members 202 can be formed from a filament or wire having a circular cross-section. Additionally, the clot engagement members 202 can be formed from a filament or wire having a non-circular cross-section. For example, filaments or wires having square, rectangular and oval crosssections may be used. In some embodiments, a rectangular wire (also known as a "flat wire") may have a height or radial dimension of between about 0.05 mm to about 0.2 mm. In some embodiments, a rectangular wire may have a width or transverse dimension of between about 0.08 mm to about 0.3 mm. In some embodiments, a rectangular wire may have a height to width ratio of between about 0.3 to about 0.9 and between about 1 and about 1.8.

Figure 4A:
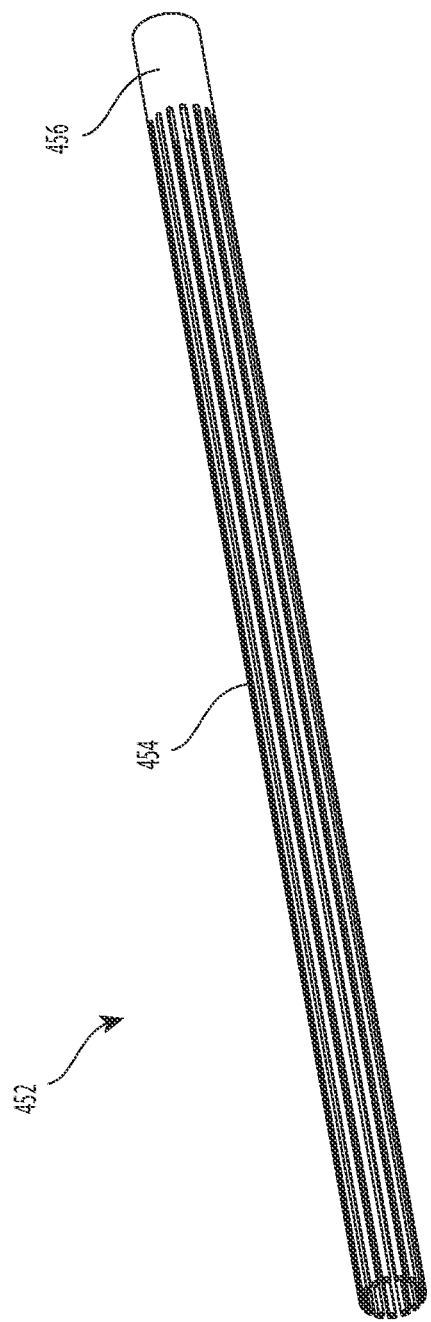
FIG. 4A is a perspective view of another embodiment of a clot treatment device in a collapsed or delivery state configured in accordance with an embodiment of the present technology.
Figure 4B:
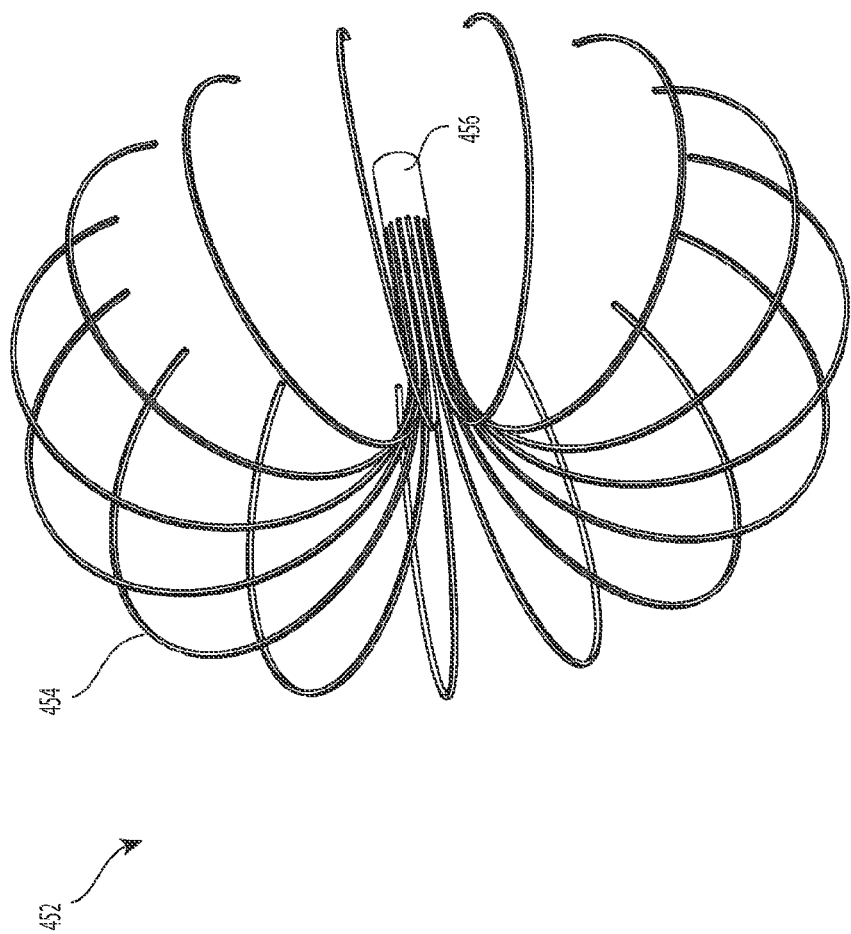
FIG. 4B is a perspective view of the clot treatment device of FIG. 4A in a deployed state configured in accordance with an embodiment of the present technology.

FIGS. 4A and 4B illustrate an embodiment in which clot engagement members having non-circular cross-sections are fabricated from a tube (e.g., a hypotube). The tube may be cut or machined by various means known in the art including conventional machining, laser cutting, electrical discharge machining (EDM) or photochemical machining (PCM). Referring to FIG. 4A, a tube may be cut to form a plurality of clot engagement members 454 that are integral with a hub member 456. The cut tube may then be formed by heat treatment to move from a delivery state shown in FIG. 4A to a deployed state shown in FIG. 4B in which an array of arcuate clot engagement members 454 project radially outward. As is known in the art of heat setting, a fixture or mold may be used to hold the structure in its desired final configuration and subjected to an appropriate heat treatment such that the clot engagement members assume or are otherwise shape-set to the desire arcuate shape. In some embodiments, the device or component may be held by a fixture and heated to about 475-525° C. for about 5-15 minutes to shape-set the structure. In some embodiments, the tubular clot engagement structure may be formed from various metals or alloys such as Nitinol, platinum, cobalt-chrome alloys, 35N LT, Elgiloy, stainless steel, tungsten or titanium.

Figure 5:
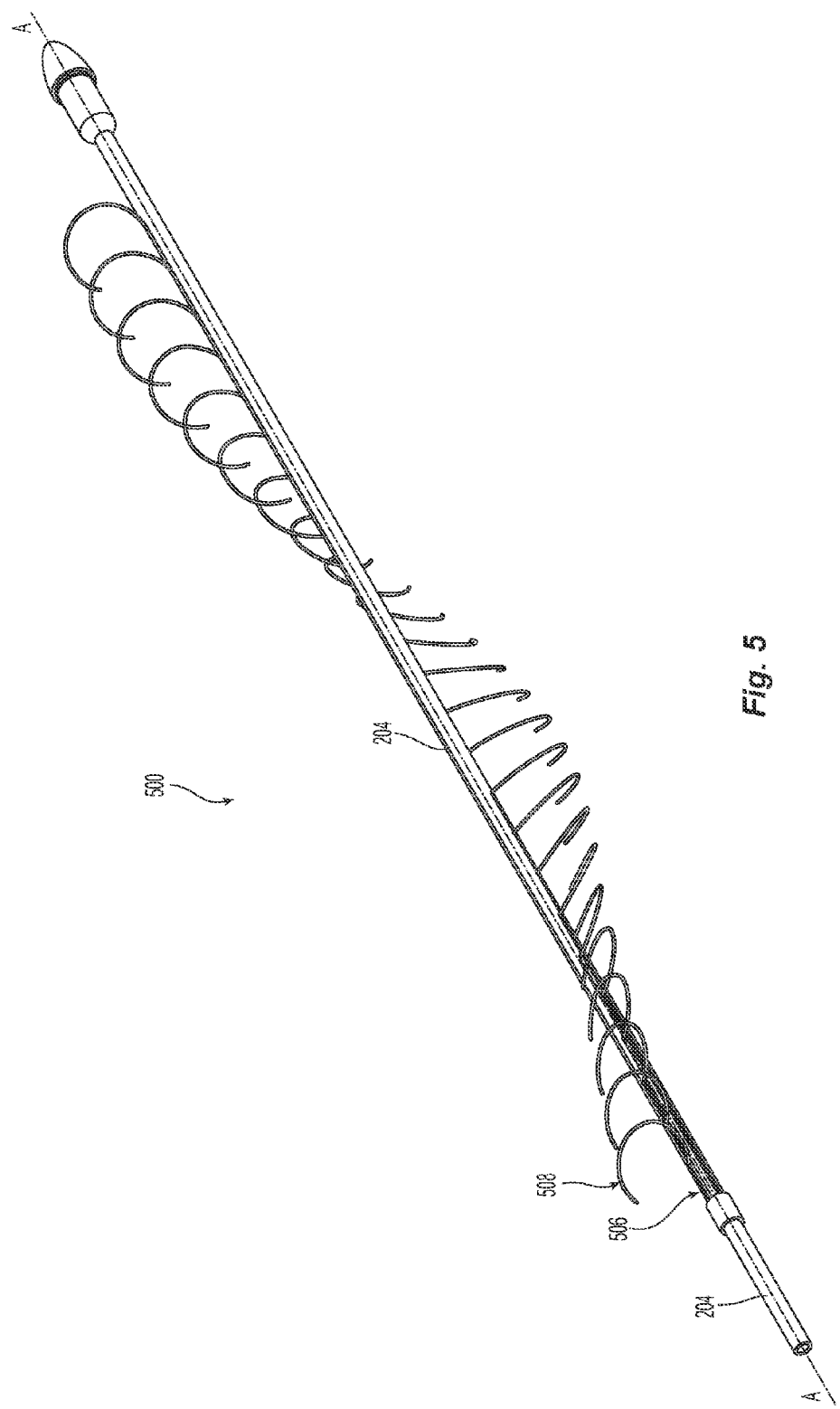
FIG. 5 is a perspective view of a clot treatment device configured in accordance with another embodiment of the present technology.

FIG. 5 is a perspective view of another embodiment of a clot treatment device 500 in a deployed state in accordance with the present technology. As shown in FIG. 5, the clot treatment device 500 can include a plurality of clot engagement members 502 generally similar to the clot engagement members 202 and 402 described with reference to FIGS. 2A-4B, except the clot engagement members 502 of FIG. 5 are arranged about the support member 204 such that the length of the first portions 506 increase in a clockwise or counterclockwise direction about 360 degrees of the support member 204. As such, the second portions 508 spiral around the length of the support member 204 and each successive second portion 508 extends from a location along the shaft that is circumferentially offset and distal to the location of the immediately adjacent second portion 508.

Figure 6:
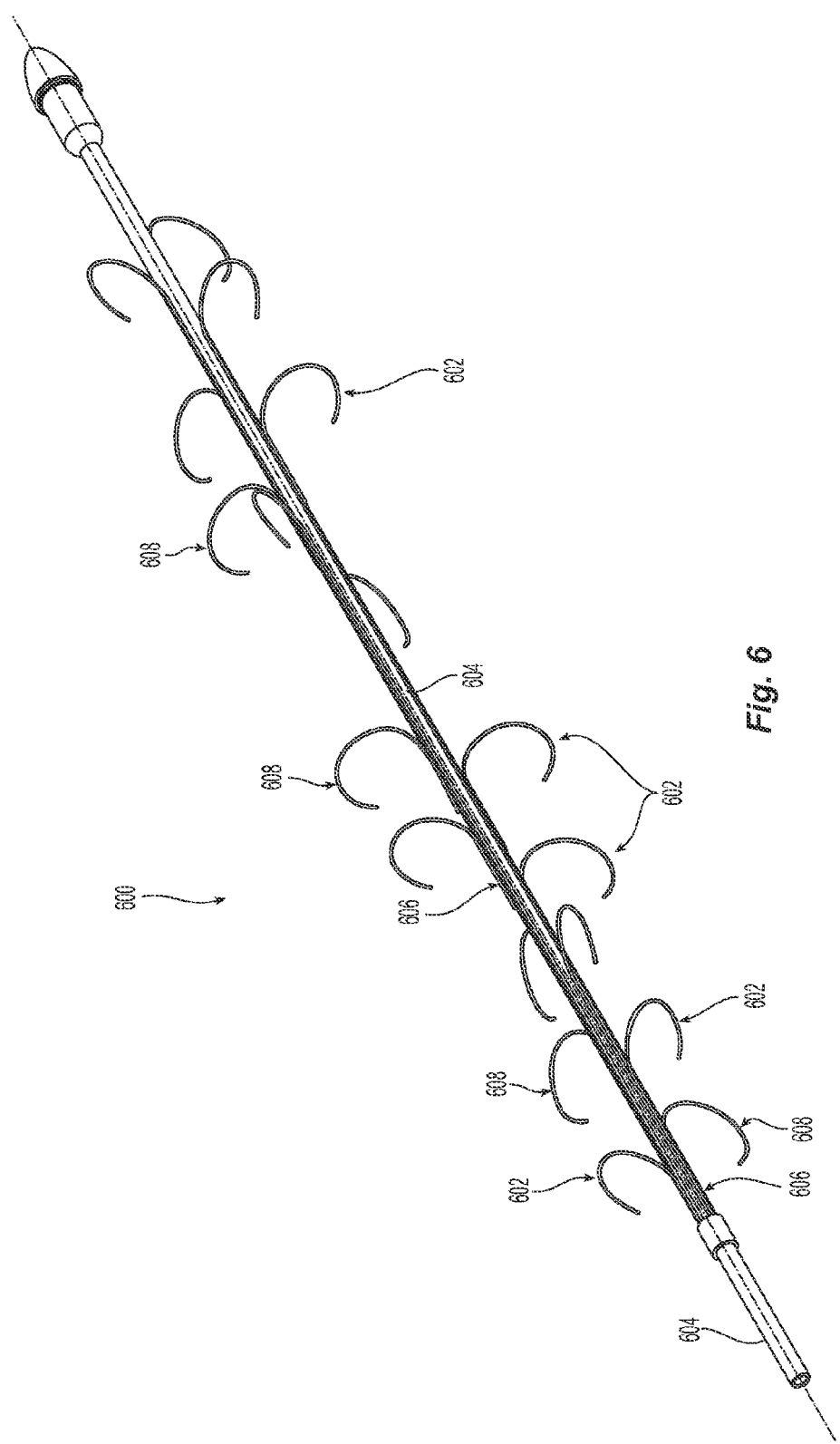
FIG. 6 is a perspective view of a clot treatment device configured in accordance with another embodiment of the present technology.

FIG. 6 is a perspective view of another embodiment of a clot treatment device 600 in a deployed state in accordance with the present technology. The clot treatment device 600 can include a plurality of clot engagement members 602 generally similar to the clot engagement members 202 and 402 described with reference to FIGS. 2A-4B, except the second portions 608 of the clot engagement members 602 of FIG. 6 are not arranged in groups, but instead extend at irregular intervals from support member 204.

Figures 7A, 7B:
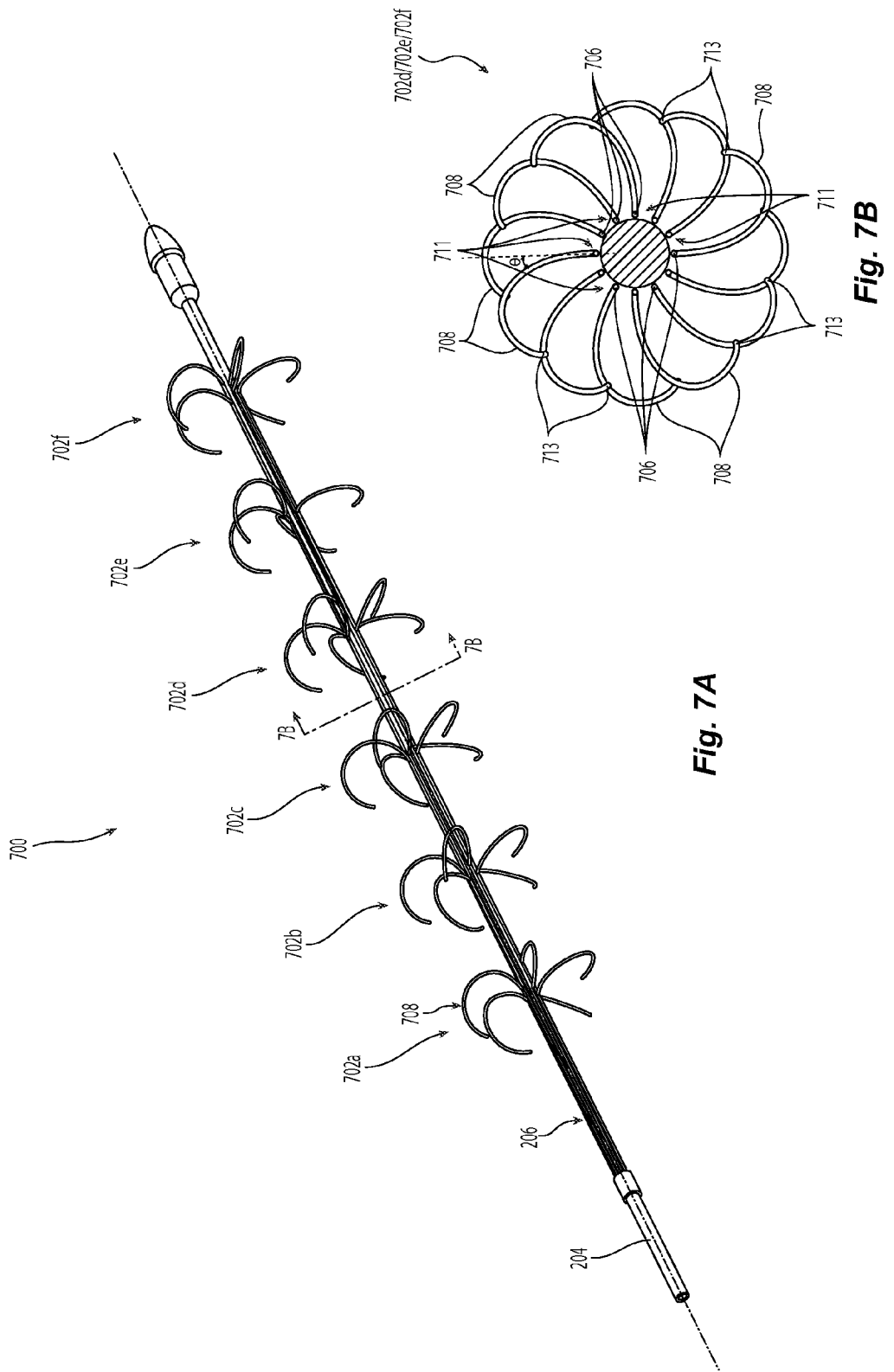
FIG. 7A is a perspective view of a clot treatment device configured in accordance with another embodiment of the present technology.
FIG. 7B is a cross-sectional end view taken along line 7B-7B in FIG. 7A.

FIG. 7A is a perspective view of another embodiment of a clot treatment device 700 in a deployed state in accordance with the present technology, and FIG. 7B is a cross-sectional end view taken along line 7B-7B in FIG. 7A. Referring to FIGS. 7A and 7B together, the clot treatment device 700 can have groups of clot engagement members 702a-f spaced along the support member 204. The groups 702a-f can include a plurality of arcuate clot engagement members 702 generally similar to the clot engagement members 202 and 402 described with reference to FIGS. 2A-4B, except the second portions 708 of the clot engagement members 702 of FIG. 7A extend at an angle from the support member 204 such that the distal ends 713 of the second portions 708 are not circumferentially aligned with the corresponding proximal ends 711 of the second portions 708. For example, as shown in FIG. 7B, the second portions 708 can extend at an angle θ from the first portions 706. In some embodiments, the angle θ can be between about 10 and about 80 degrees. In a particular embodiment, the angle θ can be between about 40 and about 60 degrees. Additionally, as shown in FIGS. 4B and 7B, the clot engagement members may form a substantially circular axial array about the axis of the support member. A circular array may engage clot more uniformly and securely than a non-circular array and thus may facilitate retrieval and removal of clot from the vessel.

Figure 8:
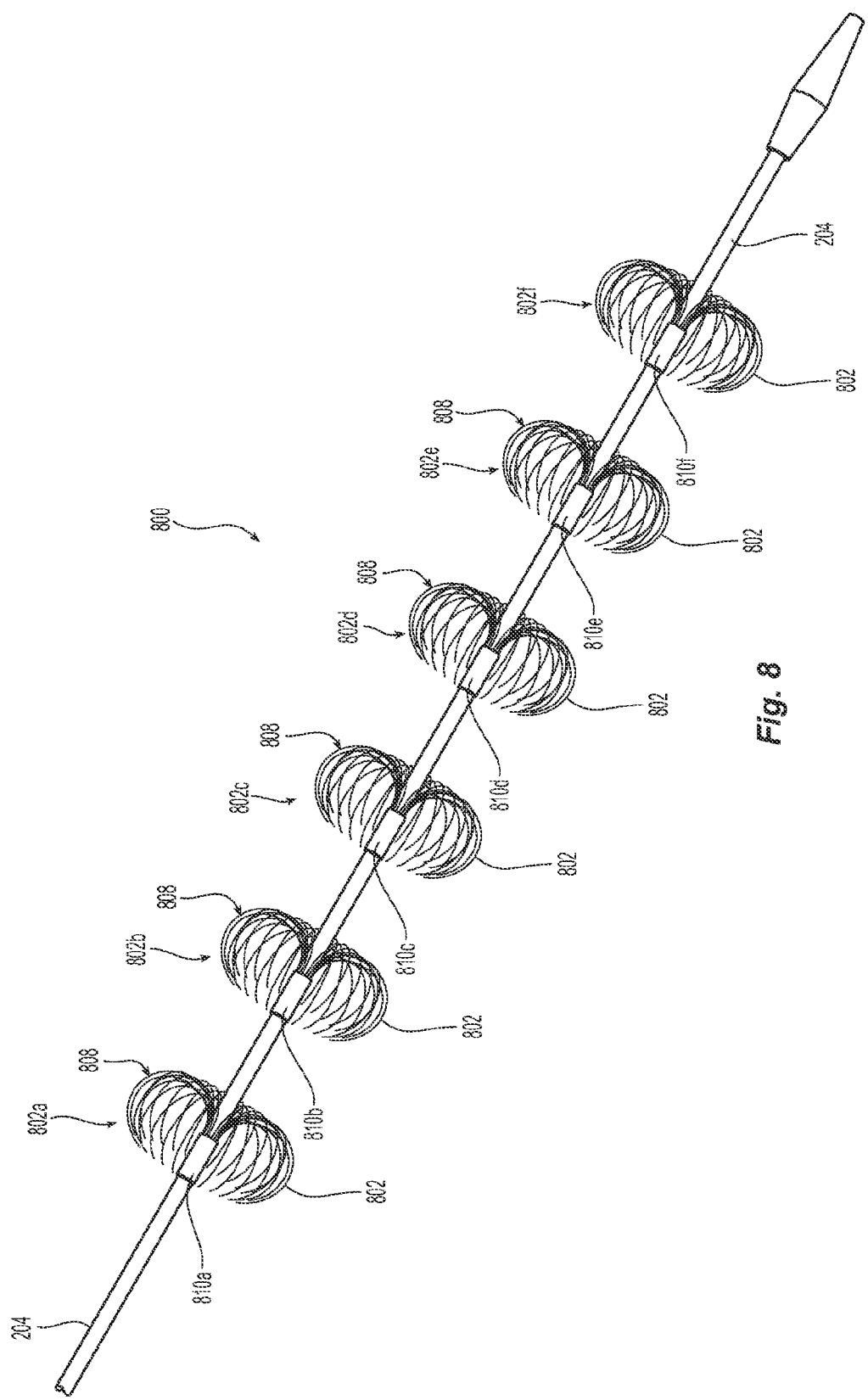
FIG. 8 is a perspective view of a clot treatment device configured in accordance with another embodiment of the present technology.

FIG. 8 is a perspective view of another embodiment of a clot treatment device 800 in a deployed state in accordance with the present technology. As shown in FIG. 8, the clot treatment device 800 can have groups of clot engagement members 802a-f spaced along the support member 204. The groups 802a-f can include a plurality of arcuate clot engagement members 802 generally similar to the clot engagement members 202 and 402 described with reference to FIGS. 2A-4B, except the clot engagement members 802 of FIG. 8 do not include a first or cantilevered portion. As such, the clot engagement members 802 include only a curved second portion 808 which is coupled to the support member 204 at one end (e.g., via hubs 810a-f). In a particular embodiment, the clot engagement members 802 can have a first portion; however, in such embodiments, the first portions of the clot engagement members 802 are relatively short (e.g., less than about 10 mm). In some embodiments, the groups 802a-f can be evenly spaced along the support member 204, and in other embodiments the groups 802a-f can have any spacing or state along the support member 204. Additionally, the arcuate clot engagement members 802 at one group 802 can have a different size than the arcuate clot engagement members 802 at a different group 802. The groups 802a-f can be deployed or expanded simultaneously (e.g., via a push-wire or other deployment methods) or consecutively (e.g., by retracting a sheath).

Figure 9A:
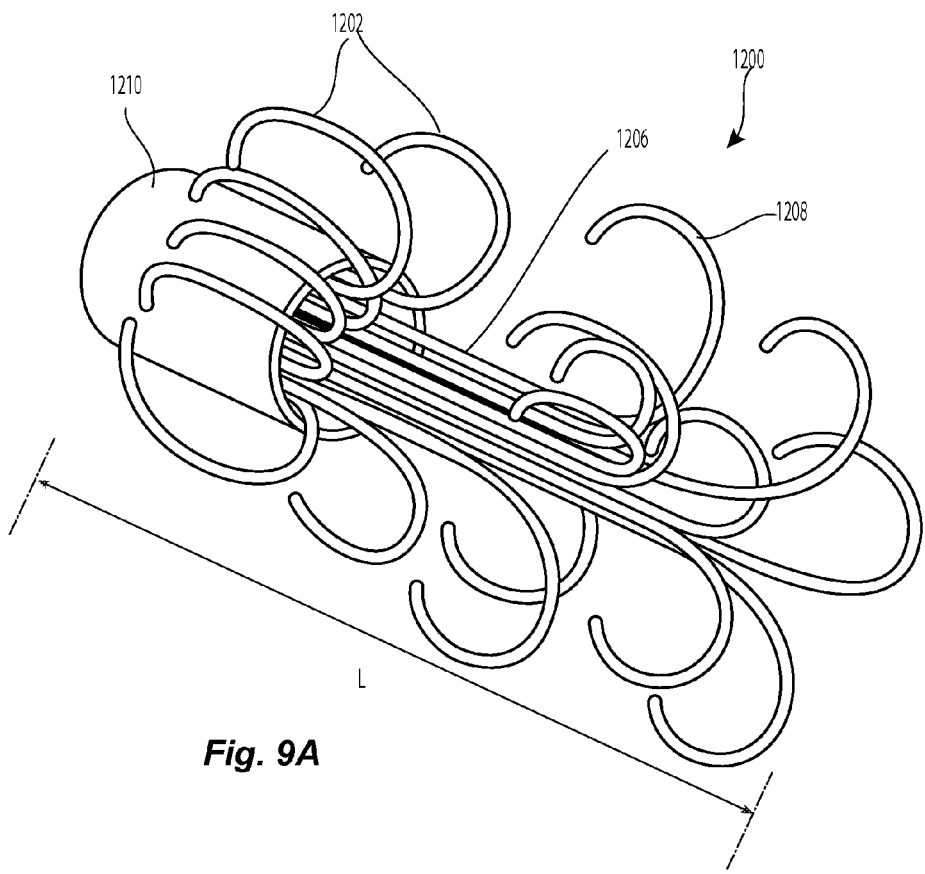
FIG. 9A is a perspective view of a clot treatment device configured in accordance with another embodiment of the present technology.
Figure 9B:
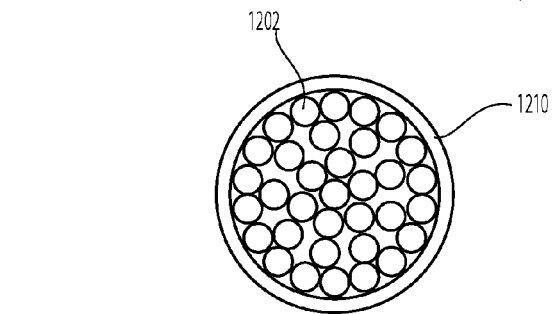
FIG. 9B is a cross-sectional end view of a portion of the clot treatment device shown in FIG. 9A.
Figure 9C:
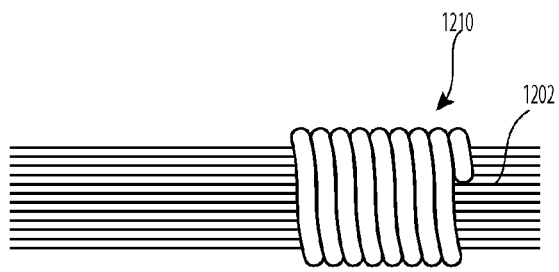
FIG. 9C is a side view of a binding member configured in accordance with the present technology.

FIG. 9A is a perspective view of another embodiment of a clot treatment device 1200 in a deployed state configured in accordance with the present technology. In some embodiments, the device 1200 can include a plurality of clot engagement members 1202 arranged in closely-packed circular array. The clot engagement members 1202 can be generally similar to the clot engagement members 202 and 402 described with reference to FIGS. 2A-4B. A proximal portion of the clot engagement members 1202 can be bound together and surrounded by a tubular binding member 1210. The clot engagement members 1202 can fill substantially all of a lumen of the binding member 1210, as shown in the cross-sectional view of FIG. 9B (other than the small gaps between the clot engagement members (that are too small for another clot engagement member)). In another embodiment (not shown), a lumen or tube may provide for passage of a guidewire or catheter through the bundle of clot engagement members. Referring to FIG. 9A, the clot engagement members 1202 can have first portions 1206 with differing lengths so that the second portions 1208 are spread out over a deployed engagement member length L. In some embodiments, the deployed engagement member length L may be between about 0.5 cm and about 8 cm, and in some embodiments, between about 1 cm and about 5 cm. As shown in FIG. 9C, the binding member 1210 can be a coil, spiral, tube, sleeve, braid and/or other generally suitable tubular configurations. The binding member 1210 may be slotted, cut or otherwise fenestrated to enhance flexibility. The binding member 1210 may be made of various metals, polymers and combinations thereof and may comprise materials visible under x-ray or fluoroscopy so as to function as a radiopaque marker to facilitate deployment, placement and retraction by the user.

II. Delivery Systems and Methods

FIG. 10 is a side partial cross-sectional view of one embodiment of a delivery system 910 for delivering the clot treatment device 200 to a treatment site, such as a pulmonary embolism. The delivery system 910 can include a proximal portion 911, an elongated delivery catheter 920 extending from a distal region of the proximal portion 911, a delivery sheath 930 slidably received within a lumen of the delivery catheter 920, a tubular push member 940 slidably received within a lumen of the delivery sheath 930, and a guidewire 912 slidably received within a lumen of the push member 940. As shown in FIG. 10, the clot treatment device 200 can be positioned within the delivery sheath 930 such that the delivery sheath 930 constrains the clot engagement members 202 in a low-profile delivery state that is generally parallel with the support member 204. In some embodiments, the delivery catheter 920 can have an outside diameter between about 0.8 mm and about 1.8 mm, and in some embodiments, between about 0.1 mm and about 0.16 mm. A proximal portion of the support member 204 can be coupled to a distal region of the push member 204 such that axial movement of the push member 204 causes axial movement of the support member 204 (and thus the clot treatment device 200).

The proximal portion 911 of the device can include a first hub 922 and a second hub 932 configured to be positioned external to the patient. The first and/or second hubs 922, 932 can include a hemostatic adaptor, a Tuohy Borst adaptor, and/or other suitable valves and/or sealing devices. A distal region 920a of the first hub 922 can be coupled to the delivery catheter 920, and a proximal region of the first hub 922 can include an opening 924 configured to slidably receive the delivery sheath 930 therethrough. In some embodiments, the first hub 922 can further include an aspiration line 926 coupled to a negative pressure-generating device 928 (shown schematically), such as a syringe or a vacuum pump. A distal region 932a of the second hub 932 can be fixed to a proximal region of the delivery sheath 930, and a proximal region of the second hub 932 can include an opening 934 configured to receive the push member 940 therethrough. Additionally, in some embodiments, the second hub 932 can include a port 936 configured to receive one or more fluids before, during and/or after the procedure (e.g., contrast, saline, etc.).

Figure 11A:
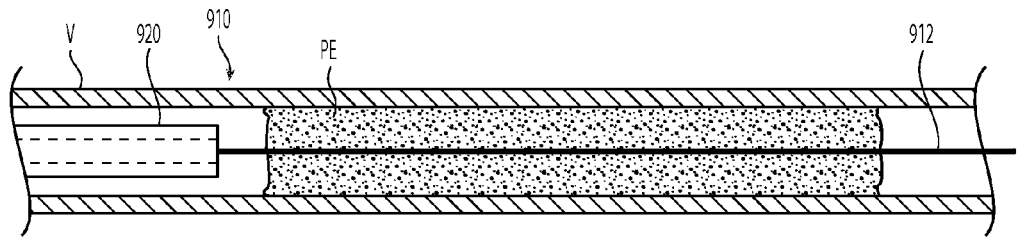
FIGS. 11A-11K illustrate a method for using a clot treatment device configured in accordance with the present technology to remove clot material from a vessel.

FIGS. 11A-11K illustrate one example for treating an embolism (e.g., a pulmonary embolism) with the clot treatment device 200 (and delivery system 910). FIG. 11A is a side view of a delivery system 910 positioned adjacent to an embolism or clot material PE within a pulmonary blood vessel V. Access to the pulmonary vessels can be achieved through the patient's vasculature, for example, via the femoral vein. The delivery system 910 can be guided through the right atrium, through the tricuspid valve, into the right ventricle, through the pulmonary valve and into the main pulmonary artery. Depending on the location of the embolism, the delivery system 910 can be guided to one or more of the branches of the right pulmonary artery and/or the left pulmonary artery. It will be understood, however, that other access locations into the venous circulatory system of a patient are possible and consistent with the present technology. For example, the user can gain access through the jugular vein, the subclavian vein, the brachial vein or any other vein that connects or eventually leads to the superior vena cava. Use of other vessels that are closer to the right atrium of the patient's heart can also be advantageous as it reduces the length of the instruments needed to reach the pulmonary embolism.

Figure 11B:
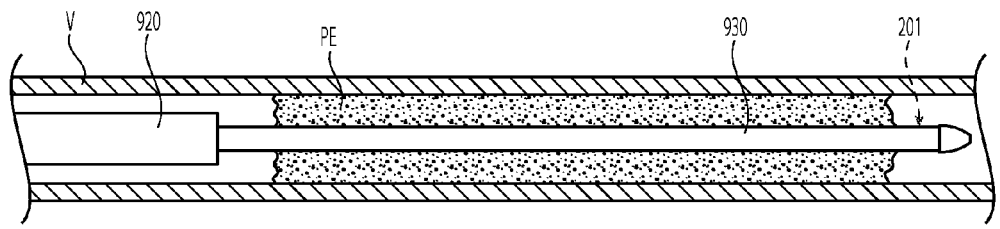
Figure 11C:
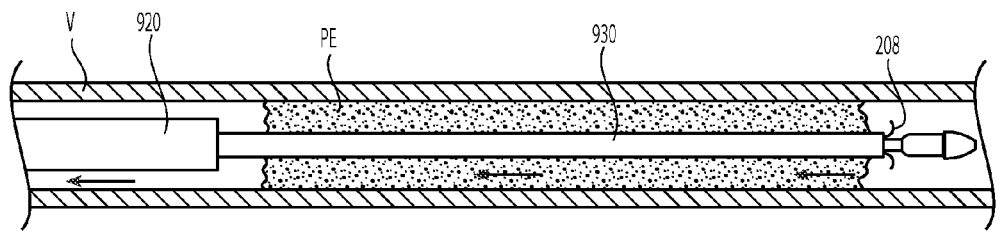
Figure 11D:
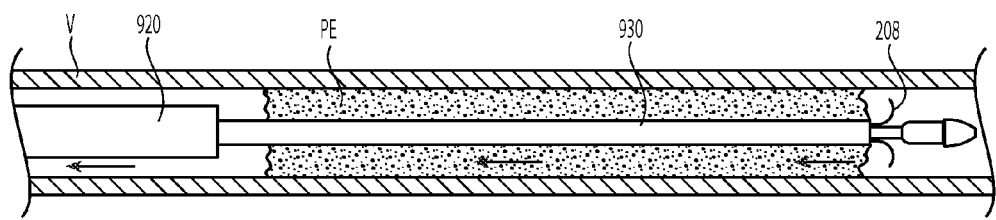
Figure 11E:
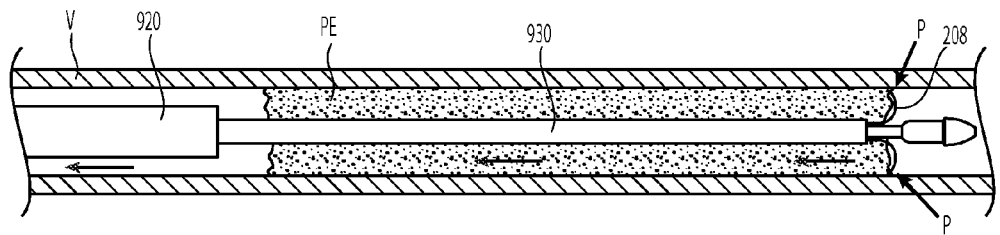

As shown in FIG. 11A, the delivery sheath 930 containing the collapsed clot treatment device 200 (not shown) can be advanced together with the delivery catheter 920 over the guidewire 912 to the treatment site. For example, the guidewire 912 can be inserted through the target pulmonary embolism PE. Referring to FIG. 11B, a distal portion of the delivery catheter 920 and/or delivery sheath 930 can then be advanced through the pulmonary embolism PE such that the distal ends 201 of at least one group of the clot engagement members 202 are aligned with or positioned distal to a distal edge of the pulmonary embolism PE. In other embodiments (not shown), a distal portion of the delivery catheter 920 and/or delivery sheath 930 can be positioned such that the distal ends 201 of at least one group of the clot engagement members 202 are positioned proximal to a distal edge of the pulmonary embolism PE.

Figure 11F:
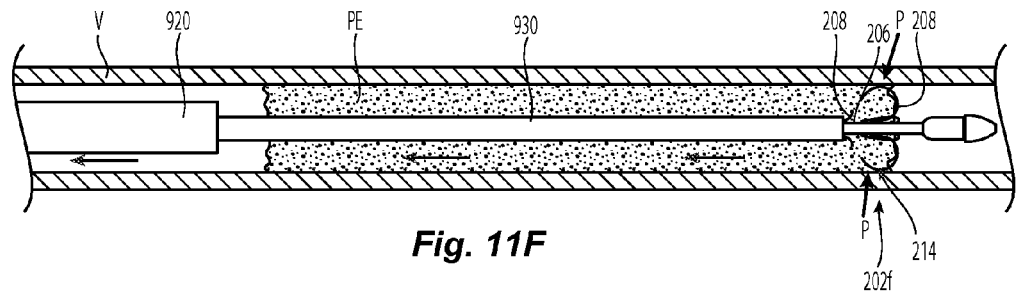

Once the device is positioned, the guidewire 912 can then be removed proximally through a lumen of the delivery sheath 930 and/or delivery catheter 920, and the delivery sheath 930 can be pulled proximally to a position proximal of the pulmonary embolism PE (as shown in FIG. 11B). As shown in FIGS. 11C-11G, the delivery sheath 930 can be retracted proximally to expose the distal portions of the second portions 208 of the clot engagement members such that the exposed portions radially expand and bend backwards in a proximal direction. As the second portions 208 expand, they extend into the pulmonary embolism PE around the device along an arcuate path P. The arcuate path P can extend radially outward and proximally with respect to the support member (not shown) and, as shown in FIG. 11F, can eventually curve radially inwardly. The second portions 208 can thus form hook-like capture elements that penetrate into and hold clot material to the device 200 for subsequent removal. Moreover, should the second portions 208 extend radially outwardly enough to touch the vessel wall, the end sections 214 of the second portions 208 form an atraumatic surface that can abut or apply pressure to the vessel wall without damaging the vessel wall. In some embodiments, the device presents a plurality of arcuate members that may be substantially parallel with the axis of the device at the point of contact with the vessel wall when in the deployed state.

Figure 11G:
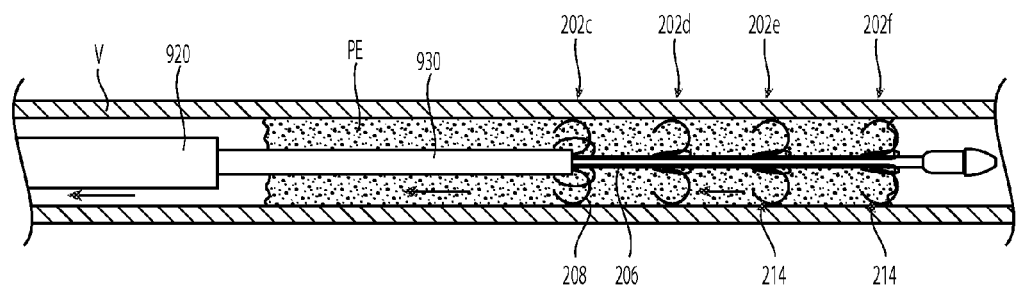
Figure 11H:
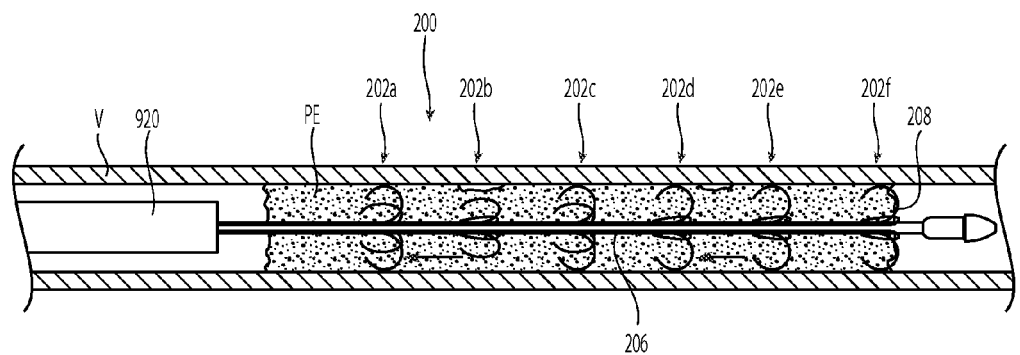
Figure 11I:
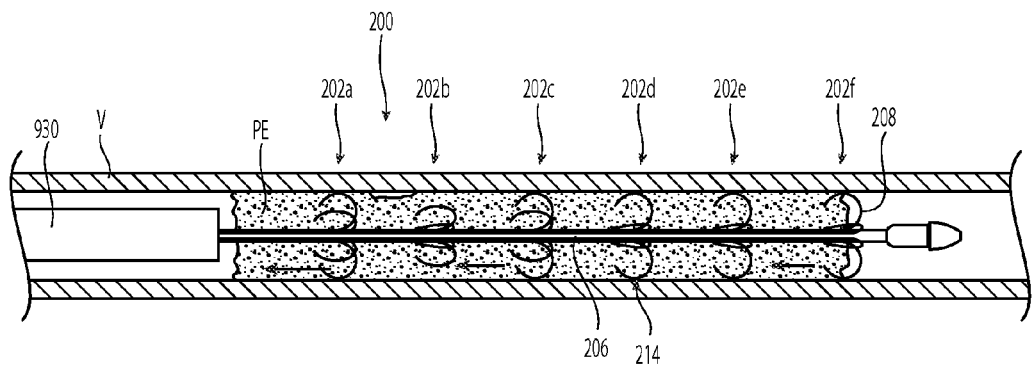
Figure 11J:
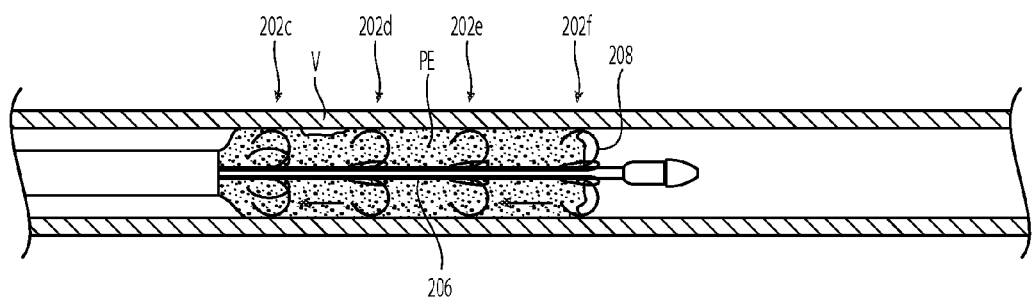

Still referring to FIG. 11F, when the delivery sheath 930 is withdrawn proximally beyond the second portions 208 of the most distal group of clot engagement members 202f, the first portions 206 of the clot engagement members 202f are exposed. In some embodiments, the delivery sheath 930 can be withdrawn so as to expose only a portion of the clot engagement members. Additionally, in those embodiments having two or more groups of clot engagement members, the delivery sheath 930 can be withdrawn to expose all or some of the groups of clot engagement members. As shown in FIG. 11G, the delivery sheath 930 can continue to be withdrawn proximally to expose additional second portions 208 and/or groups of clot engagement members 202a-f. Clot engagement members 202a-f may just contact or be slightly deflected by the vessel wall. If the device is sized such that the diameter of the clot engagement members are larger than the vessel diameter (e.g., "over-sized"), the clot engagement members may be compressed by the vessel wall. Thus, while fully deployed, the device may be in state of a small amount of radial compression. In some embodiments, the device may be diametrically over-sized by between about 5% and 50% and in other embodiments between about 10% and 25%.

As shown in FIGS. 11H-11K, once at least a portion of the clot engagement members and/or second portions 208 have penetrated and engaged the targeted clot material PE, the clot treatment device 200 can be withdrawn proximally, thereby pulling at least a portion of the clot material PE in a proximal direction with the device 200. For example, the push member 940, second hub 932, and delivery sheath 930 (FIG. 10) can be retracted proximally at the same time and rate. As such, the delivery catheter 920 can be held in place while the delivery sheath 930, clot material PE, and clot engagement device 200 are pulled proximally into the delivery catheter 920. The curved shape of the second portions 208 increases the surface area of the clot engagement members 202 in contact with the clot material PE, thus increasing the proximal forces exerted on the clot material. Withdrawal of the device 200 not only removes the clot but also can increase blood flow through the vessel.

Figure 11K:
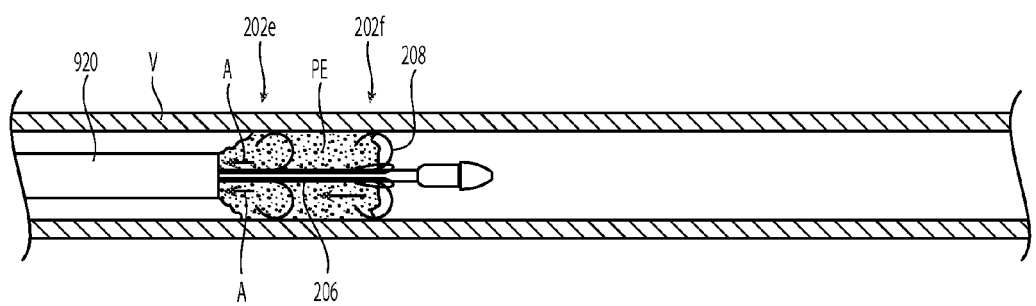

As shown in FIG. 11K, in some embodiments the delivery catheter 920 can include an aspiration lumen (not shown) configured to apply a negative pressure (indicated by arrows A) to facilitate removal of the clot material PE. For example, the delivery catheter 920, delivery sheath 930 and/or clot treatment device 200 of the present technology can be configured to be operably coupled to the retraction and aspiration apparatus, titled "Retraction and Aspiration Apparatus and Associated Systems and Methods," filed concurrently herewith, which is incorporated herein by reference in its entirety.

When coupled to the retraction and aspiration apparatus, a negative pressure is applied at or near the distal portion of the delivery catheter 920 (via the aspiration lumen) only while the clot treatment device 200 and/or delivery sheath 930 is being retracted. Therefore, when retraction pauses or stops altogether, aspiration also pauses or stops altogether. Accordingly, aspiration is non-continuous and dependent upon retraction of the delivery sheath 930 and/or clot treatment device 200. Such non-continuous, synchronized aspiration and retraction can be advantageous because it reduces the amount of fluid withdrawn from the patient's body during treatment (and thus less fluid need be replaced, if necessary). In addition, it may be advantageous to consolidate the steps and motions required to both mechanically transport thrombus into the guide catheter (e.g. aspiration tube) and remove fluid from the tube into one motion, by one person.

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

We claim:

1. A method of treating an embolism that at least partially restricts blood flow through a vessel, the method comprising:
   deploying an embolectomy device within the embolism, wherein—
   the embolectomy device includes a first plurality of clot engagement members configured to deploy at a first location along the device and a second plurality of clot engagement members configured to deploy at a second location along the device proximal of the first location, and
   the embolectomy device is deployed by withdrawing a delivery catheter such that—
   a terminus of at least one of the clot engagement members of the first and/or second pluralities of clot engagement members penetrates through the clot material along an arcuate path that extends radially outward, then proximally with respect to the elongated shaft, and then curves radially inwardly, whereby the clot material is held by at least one of the clot engagement members of the first and/or second pluralities of clot engagement members, and
   at least one of the first plurality of clot engagement members penetrates through the clot material at the first location and, upon further withdrawal of the delivery catheter, at least one of the second plurality of clot engagement members penetrates through the clot material at the second location;
   moving the embolectomy device and at least a portion of the embolism along the vessel; and
   withdrawing the embolectomy device and at least a portion of the embolism from the vessel.

2. The method of claim 1 wherein deploying the embolectomy device comprises expanding at least one clot engagement member of the first and/or second pluralities of clot engagement members into arcuate shapes, each having a concave portion facing proximally.

3. The method of claim 1 wherein withdrawing the embolectomy device comprises urging the portion of the embolism into a catheter while applying a vacuum through the catheter.

4. The method of claim 3 wherein the vacuum applied through the delivery catheter is synchronized with withdrawal of the embolectomy device into the delivery catheter.

5. The method of claim 1 wherein withdrawing the embolectomy device includes extracting at least some clot material and thereby increasing flow in the blood vessel where flow had been reduced by the presence of a thrombus.

6. The method of claim 1 further comprising treating a pulmonary embolism with the embolectomy device.

7. The method of claim 6 wherein each clot engagement member of the first and second pluralities of clot engagement members has a first portion and a second portion extending from the first portion, and wherein the first portion has a proximal region attached to a support member and a distal region, and wherein the first portion extends distally in a longitudinal direction from the proximal region to the distal region.

8. The method of claim 7 wherein the second portion further includes an end section curving radially inward from the proximally extending section.

9. The method of claim 6 wherein each clot engagement member of the first and second pluralities of clot engagement members has a proximal region that is fixed to a distal portion of the embolectomy device.

10. The method of claim 1 wherein each clot engagement member of the first and/or second pluralities of clot engagement members has a plurality of microfeatures configured to facilitate adhesion of thrombus.

11. The method of claim 1 wherein each clot engagement member of the first and/or second pluralities of clot engagement members is coated to promote adhesion of thrombus.

12. The method of claim 1 wherein each clot engagement member of the first and/or second pluralities of clot engagement members defines an arc length that is between about 200 degrees and 340 degrees.

13. The method of claim 1 wherein each clot engagement member of the first and/or second pluralities of clot engagement members has a non-circular cross-section and is fabricated from a tube.

* * * * *

UNITED STATES PATENT AND TRADEMARK OFFICE
CERTIFICATE OF CORRECTION

PATENT NO. : 9,259,237 B2  
APPLICATION NO. : 14/299933  
DATED : February 16, 2016  
INVENTOR(S) : Richard Quick et al.

It is certified that error appears in the above-identified patent and that said Letters Patent is hereby corrected as shown below:

On the title page, in item (56), in column 1, under "Other Publications", line 2, delete "coronay" and insert -- coronary --, therefor.

Signed and Sealed this
Fourteenth Day of June, 2016

Michelle K. Lee
*Director of the United States Patent and Trademark Office*